(12) United States Patent
Anschutz et al.

(10) Patent No.: US 7,121,156 B2
(45) Date of Patent: Oct. 17, 2006

(54) PROPPANT SAMPLING

(75) Inventors: Donald A. Anschutz, Houston, TX (US); John G. Wick, Cypress, TX (US)

(73) Assignee: Proptester, Inc., Cypress, TX (US)

( * ) Notice: Subject to any disclaimer, the term of this patent is extended or adjusted under 35 U.S.C. 154(b) by 0 days.

(21) Appl. No.: 11/048,304

(22) Filed: Jan. 31, 2005

(65) Prior Publication Data

US 2006/0169064 A1    Aug. 3, 2006

(51) Int. Cl.
  *G01N 1/20*    (2006.01)
(52) U.S. Cl. .................................... 73/863.61
(58) Field of Classification Search ............. 73/863.61
See application file for complete search history.

(56) References Cited

U.S. PATENT DOCUMENTS

| | | | |
|---|---|---|---|
| 406,447 A | 7/1889 | Kennedy, Jr. | |
| 3,367,603 A | 2/1968 | Feyerherd | |
| 3,701,496 A | 10/1972 | Ekama | |
| 3,750,478 A * | 8/1973 | Keene | 73/863.44 |
| 3,762,664 A | 10/1973 | Loveless | |
| 3,834,418 A | 9/1974 | Clancy | |
| 3,868,071 A | 2/1975 | Weaver | |
| 3,961,643 A | 6/1976 | Lynch | |
| 4,056,983 A * | 11/1977 | Mazzetti | 73/863.44 |
| 4,138,161 A | 2/1979 | Payne | |
| 4,355,930 A | 10/1982 | Carlier | |
| 4,732,512 A | 3/1988 | Welch | |
| 4,944,905 A * | 7/1990 | Gibb et al. | 264/660 |
| 5,226,759 A | 7/1993 | Hilmer et al. | |
| 5,309,773 A * | 5/1994 | Tokoyama | 73/863.01 |
| 5,741,094 A | 4/1998 | Heep | |
| 5,988,951 A | 11/1999 | DiFrank et al. | |
| 6,709,203 B1 | 3/2004 | McKinnis | |

\* cited by examiner

*Primary Examiner*—Hezron Williams
*Assistant Examiner*—Paul M. West
(74) *Attorney, Agent, or Firm*—Streets & Steele; Jeffrey L. Streets

(57) ABSTRACT

Methods and systems useful for obtaining a representative sample of solid particles from a pneumatically conveyed stream of solid particles. One preferred method and system includes establishing a pneumatic flow of solid particles in a gas stream through a sampling conduit and diverting the steam through a second conduit; isolating an inlet of the sampling conduit from the second conduit substantially simultaneously with the step of diverting the entire stream through the second conduit and emptying material from the isolated sampling conduit, wherein the representative sample comprises the material emptied from the sampling conduit. The outlet end of the sampling conduit may be vented into the second conduit or the atmosphere. The system for accomplishing the method may include a controller for controlling, inter alia, a position of the means for diverting the stream through a second conduit, the means for isolating an inlet sampling conduit, or combinations thereof.

7 Claims, 6 Drawing Sheets

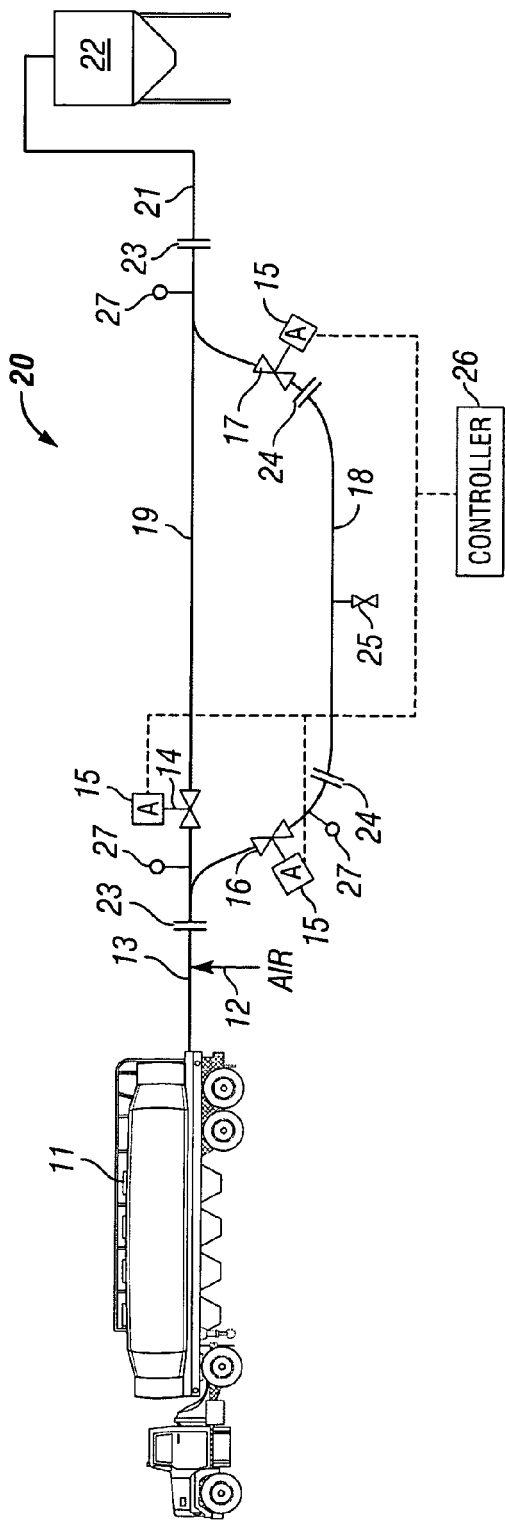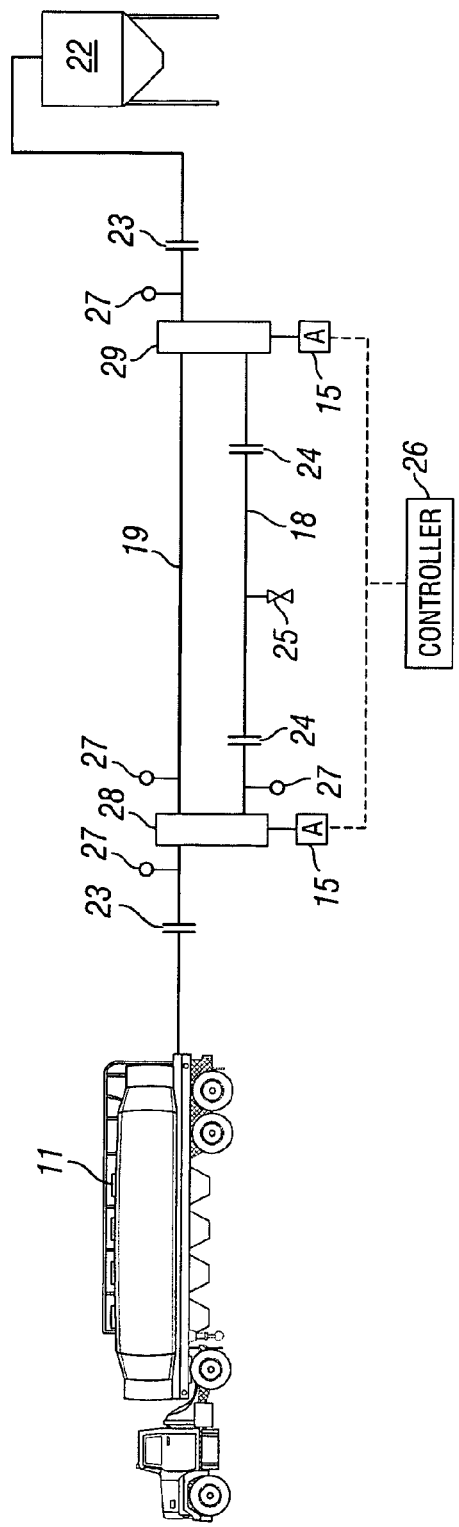

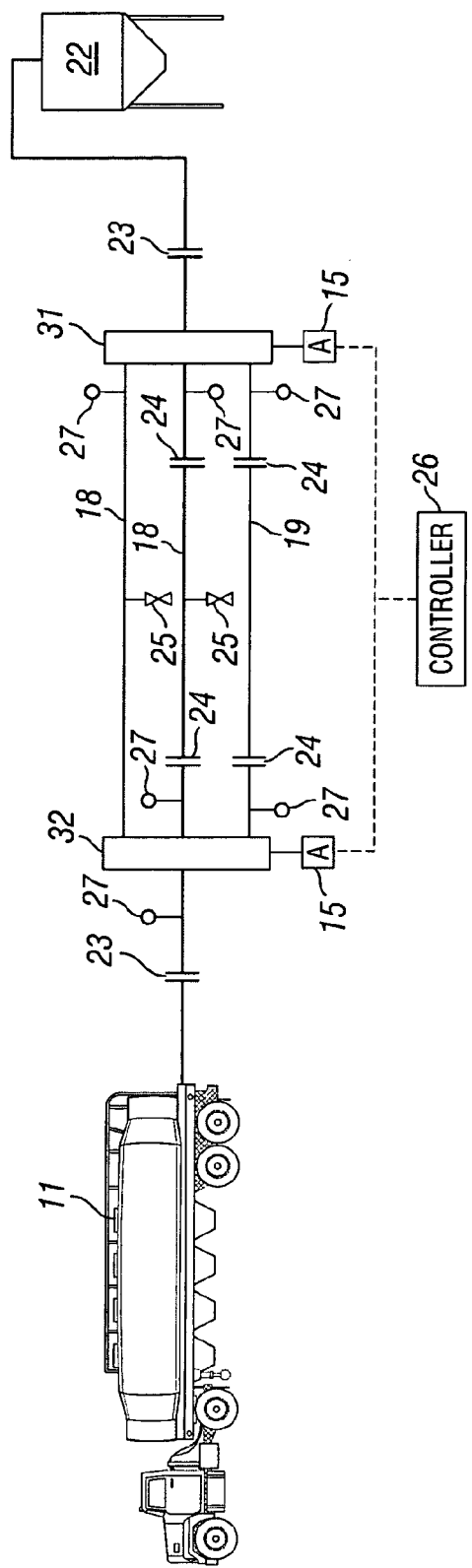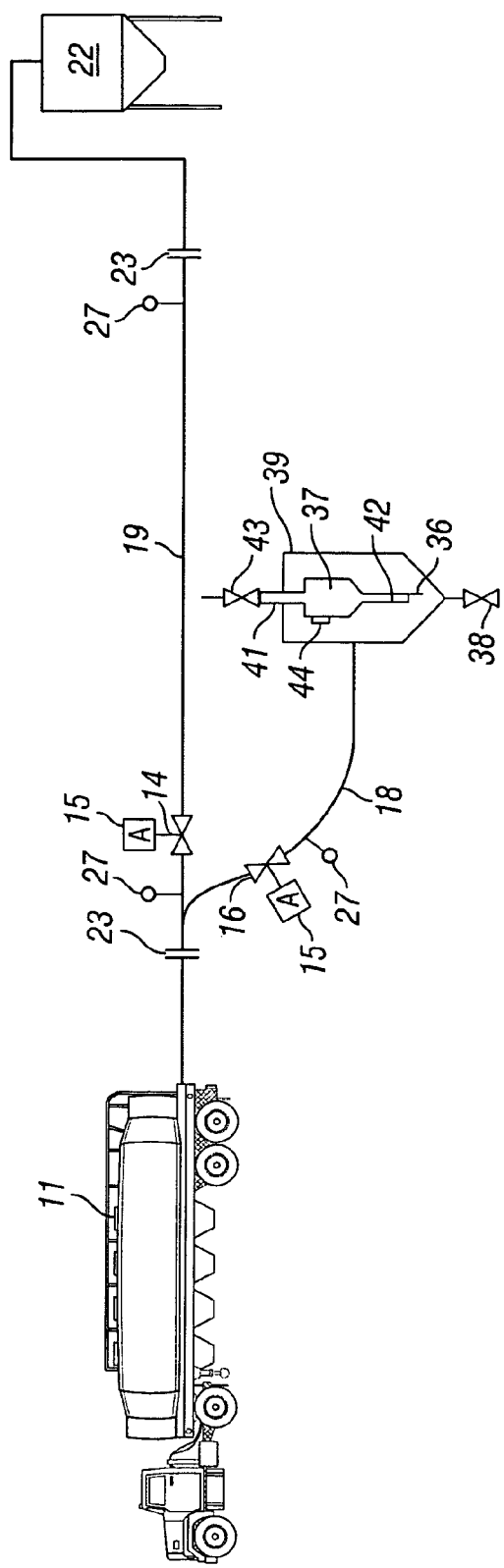

PROPPANT SAMPLING

BACKGROUND OF THE INVENTION

1. Field of the Invention

This invention relates generally to the field of solids handling and more particularly, to methods and apparatus useful for procuring a representative sample of pneumatically conveyed solid particles.

2. Description of the Related Art

Oil and natural gas are produced from wells having porous and permeable subterranean formations. The porosity of the formation permits the formation to store oil and gas, and the permeability of the formation permits the oil or gas fluid to move through the formation. Sometimes the permeability of the formation holding the gas or oil is insufficient for economic recovery of oil and gas. In other cases, during operation of the well, the permeability of the formation drops to such an extent that further recovery becomes uneconomical. In such circumstances, it is common to fracture the formation and prop the fracture in an open condition by means of a proppant material or propping agent. Fracturing is usually accomplished by hydraulic pressure using a gel-like fluid. The pressure is increased until cracks form in the underground rock. The proppants, which are suspended in this pressurized fluid, are forced into the cracks or fissures. When the hydraulic pressure is reduced, the proppant material functions to prevent the formed fractures from closing again by "propping" the fractures open.

A wide variety of proppant materials are used, depending on the geological conditions. Typically, proppants are particulate materials, such as sand, glass beads, or ceramic pellets, which create a porous structure. Often, the proppants are coated with a resin to improve vital physical characteristics of the proppants. The oil or gas is able to flow through the interstices between the particles to collection regions, from which it is pumped to the surface. Over time, the pressure of the surrounding rock tends to crush the proppants. The resulting fines from this disintegration tend to migrate and plug the interstitial flow passages in the propped structure. These migratory fines drastically reduce the permeability, lowering the conductivity of the oil or gas. Conductivity is a measure of the deliverability or the ease with which oil or gas can flow through the proppant structure and is important to the productivity of a well. When the conductivity drops below a certain level, the fracturing process is repeated or the well is abandoned.

There are many physical characteristics of proppants that are important. Particle size of the proppant has a significant impact on the permeability, and resulting ability for hydrocarbon flow through the fracture, of the proppant pack. Crush strength of the proppant is another vital physical characteristic of the proppant because the proppant is subjected to high pressure levels as they prop open the fracture. Early proppants were formed of materials such as sand, glass beads, walnut shells, and aluminum pellets. However, where closure pressures of the fracture exceed a few thousand pounds per square inch these materials are crushed resulting in a closure of the fracture. In response, proppants having high compressive strength have been designed to resist crushing under the high pressure levels experienced in use. The crush strength of the proppants is related to the composition and density of the proppant material. Another important physical characteristic of the proppant is the shape of the individual particle, wherein roundness and a high level of sphericity are important characteristics.

The importance of the physical characteristics of proppants is well recognized in the industry. The American Petroleum Institute (API) has issued Recommended Practices for proppant testing. For example, API Recommended Practices RP-56 covers testing procedures for sand used in hydraulic fracturing operations. RP-58 provides testing procedure for sand used in gravel packing operations. RP-60 provides testing procedures for high-strength proppants used in hydraulic fracturing operations. These Recommended Practices include testing procedures for determination of properties that include, inter alia, particle size, crush resistance and sphericity and roundness.

Correct sampling technique of the proppants while gathering representative samples for testing is critical. If an improper sampling technique is used, a sample of the proppant gathered for laboratory analysis may not be representative of the entire proppant population being tested and the laboratory results will not provide the true physical characteristics of the proppant. The API Recommended Practices RP-56, RP-58 and RP-60 all include instructions for sampling proppants from the source of supply that include obtaining the samples by sweeping a collection device across the entire delivery stream as the proppants fall from a conveyer belt into a blender or other destination. Grabbing a sampling from a loaded silo or hopper does not provide a representative sample of the proppant.

Typically, proppants are delivered in bulk to the drilling site by trucks or railcar and unloaded pneumatically from the transport to a silo or hopper for storage until needed for injection during the fracturing procedure. When needed, the proppants flow by gravity from the silo to a mixer or blender to produce the fracturing liquid for injection into the reservoir. Unfortunately, the representative samples of the proppant that are tested are collected by using the sweeping collection device just as the proppant falls into the blender on its way to be injected as part of a well fracturing analysis. By the time the laboratory analyses are run on these representative samples of proppants at the drilling site, the proppants have already been injected into the reservoir. While the laboratory results of the proppant sample caught just before the proppant was mixed into the fracturing liquid document that a problem with the proppant existed, the results are too late to correct the problem by replacing the poor quality proppant with new proppant having the required physical characteristics.

What is needed is a method and apparatus for collecting a representative sample of the bulk proppant before the proppant is needed for injection. It would be beneficial if the representative sample of the proppant could be collected as it was being delivered off the transport truck or railcar.

SUMMARY OF THE INVENTION

The present invention provides methods and apparatus useful for obtaining a representative sample of solid particles from a pneumatically conveyed stream of solid particles. In one preferred method, the steps include establishing a pneumatic flow of solid particles in a gas stream through a sampling conduit and diverting the steam through a second conduit. The method further includes isolating an inlet of the sampling conduit from the second conduit substantially simultaneously with the step of diverting the entire stream through the second conduit and emptying material from the isolated sampling conduit, wherein the representative sample comprises the material emptied from the sampling conduit.

A preferred embodiment of a method for obtaining a representative sample further includes, as part of the step of establishing the flow through the sampling conduit, venting an outlet end of the sampling conduit into the second conduit. The step of isolating the sampling conduit fro the second conduit may further include isolating the outlet end of the sampling conduit from the second conduit.

In an alternate embodiment, the step of establishing the flow through the sampling conduit may further include venting an outlet of the sampling conduit into the atmosphere through a solids separation device. This step may further include capturing solids from a gas stream vented from the solids separation device, wherein the representative sample comprises the solids captured by the solids separation device.

A system of the present invention provides the apparatus suitable for implementing the method of the present invention. One preferred embodiment of the system includes a sampling conduit adapted for establishing a pneumatic flow of solid particles in a gas stream through the sampling conduit and means for diverting the entire stream through a second conduit. The embodiment further includes means for isolating an inlet of the sampling conduit from the second conduit substantially simultaneously with activating the means for diverting the entire stream through the second conduit and means for emptying material from the isolated sampling conduit, wherein the representative sample comprises the material emptied from the sampling conduit.

A preferred embodiment of the system for obtaining a representative sample of a pneumatically conveyed stream of solid particles may further include means for venting an outlet end of the sampling conduit into the second conduit and/or means for isolating the outlet end of the sampling conduit from the second conduit. Alternatively, for an embodiment that includes venting the sampling conduit to the atmosphere, the system may further include a solids separation device for capturing the solid particles carried from the outlet of the sampling conduit vented to the atmosphere. This system may further include means for capturing solids from a gas stream vented from the solids separation device, wherein the representative sample comprises the solids captured by the solids separation device and the solids captured by the means for capturing solids from the gas stream vented from the solids separation device.

In a preferred embodiment, the invention further includes a controller for controlling a position of the means for diverting the stream through a second conduit, the means for isolating an inlet sampling conduit, or combinations thereof.

The present invention further provides a diverter for diverting a pneumatically conveyed stream of solid particles. In one embodiment, the diverter includes a slide comprising an opening therethrough and a slide nozzle mounted circumferentially around the opening on a first side of the slide, the slide being slidingly disposed between a first flange and a second flange to provide selective fluid communication through the opening between the first flexible conduit on a first end of the diverter and two or more nozzles on a second end of the diverter. The diverter may further include an actuator coupled to the slider for positioning the slider and/or a sealing plate disposed between the slide and the second flange for providing a fluid seal between the opening through the slide and the sealing plate.

In a preferred embodiment of the present invention, a diverter includes a slide comprising an opening therethrough, the slide being slidingly disposed between a first flange and a second flange to provide selective fluid communication through the opening between the first flexible conduit on a first end of the diverter and two or more nozzles on a second end of the diverter. The diverter may further include a housing having the first flange mounted on a first end of the housing and the second flange mounted on a second end of the housing, wherein the housing is adapted for being pressurized to a housing pressure higher than a stream pressure of the pneumatically conveyed stream of solid particles.

The foregoing and other objects, features and advantages of the invention will be apparent from the following more particular description of a preferred embodiment of the invention, as illustrated in the accompanying drawings wherein like reference numbers represent like parts of the invention.

BRIEF DESCRIPTION OF THE DRAWINGS

FIG. 1 is a schematic drawing of a system for collecting a representative sample of a pneumatically conveyed stream of solid particles having a sampling conduit vented to the receiving vessel fill line.

FIG. 2 is a schematic drawing of a system similar to the one shown in FIG. 1 but having optional diverters instead of valves.

FIG. 3 is a schematic drawing of a system similar to the one shown in FIG. 1 but having two sampling conduits.

FIG. 4 is a schematic drawing of a system for collecting a representative sample of a pneumatically conveyed stream of solid particles having a sampling conduit vented to the atmosphere.

DETAILED DESCRIPTION OF PREFERRED EMBODIMENTS

Figure 5:
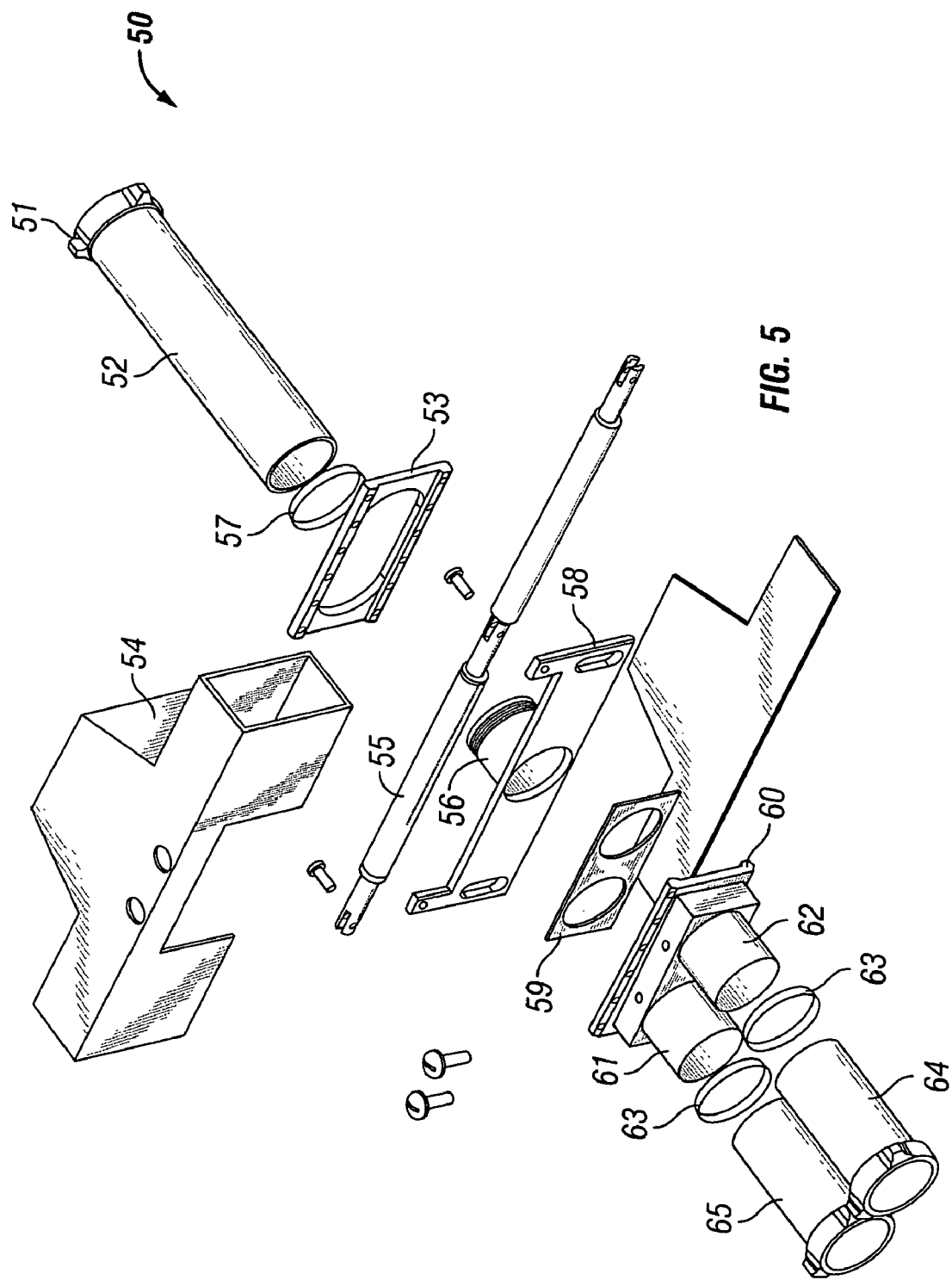
FIG. 5 is an expanded view of a diverter useful for implementing the method and system of the present invention.

The present invention provides methods and devices for capturing a representative sample of a stream of solid particles that are being pneumatically conveyed through a conduit. Capturing a representative sample of the pneumatically conveyed sample cannot be obtained by merely opening a sampling valve on the line and filling a sample container with the material that flows out of the sampling valve. A sample thus obtained is typically not representative of all the material flowing through the conduit. The present invention provides a solution to the problem of capturing representative samples of pneumatically conveyed solids flowing through a conduit.

Pneumatic conveyance as used herein includes transporting solid particles through a conduit with a carrier gas that is typically, but not limited to, air. Other gases, for example nitrogen or carbon dioxide, or mixtures of gases may also be used as necessary or convenient for a given application. Furthermore, while the following discussion is directed towards a pneumatically conveyed stream of proppants that are useful in the oil and gas well industry, the present invention is useful as well for capturing a representative sample of other pneumatically conveyed solid materials including, for example, grains, other agricultural products, pelletized plastics, catalysts and granular or pelletized chemicals. The discussion of proppants that follows is by way of example only and is not meant to limit the scope of the present invention to proppants in any manner.

To capture a representative sample of the pneumatically conveyed stream of solid particles, it is desirable to establish the flow of the entire stream through a sampling conduit and then to isolate the sampling conduit, thereby capturing the representative sample that comprises the captured material. Alternatively, if capturing only a portion of the entire flowing stream will provide a representative sample, only the flow of a portion of the entire steam need be established through the sampling conduit.

Proppants are typically delivered to a well site by rail car, truck, barge or other delivery vessel and are unloaded pneumatically through a fill conduit into a hopper or other receiving vessel for use during the well fracturing procedure. Conventionally, the operator establishes a connection between the unloading conduit from the delivery vessel and the filling conduit of the receiving vessel to begin the unloading process into the hopper.

In a preferred embodiment of the present invention, a method is provided for obtaining a representative sample from a pneumatically conveyed stream of solid particles. The method includes establishing a pneumatic flow of solid particles in a gas stream through a sampling conduit and then isolating the sampling conduit to capture the representative sample that comprises the material captured in the sampling conduit. The inlet to the sampling conduit is adapted for being in selective fluid communication with the unloading conduit from the delivery vessel so that the full flow of the pneumatically conveyed stream of solid particles being unloaded from the delivery vessel can be directed through the sampling conduit. In a preferred embodiment, the inlet to the sampling conduit is as close to the inlet of the receiving vessel as possible so that any damage inflicted upon the proppant as a result of flowing through the conduit can be found in the representative sample. Optionally, as stated above, if capturing only a portion of the entire flowing stream will provide a representative sample, only the flow of a portion of the entire steam need be established through the sampling conduit.

After the flow of the entire pneumatically conveyed stream is flowing through the sampling conduit, or only a portion of the stream if that provides a representative sample, the method includes diverting the entire stream though a second conduit and optionally, substantially simultaneously isolating the sampling conduit from the second conduit at both the inlet and outlet of the sampling conduit. These steps occur with very little or no interruption to the flow of the pneumatically conveyed steam as the proppant continues to be unloaded from the delivery vessel. The second conduit is adapted for being in selective fluid communication with the unloading conduit of the delivery vessel and also with the inlet of the filling conduit of the receiving vessel so that the full flow of the pneumatically conveyed stream of solid particles may be unloaded into the receiving vessel while the sampling conduit is isolated.

In a preferred embodiment of the method, the method further includes venting an outlet end of the sampling conduit into the filling conduit of the receiving vessel as part of the step of establishing the pneumatically conveyed stream of solid particles through the sampling conduit. Since the inlet of the sampling conduit is in selective fluid communication with the unloading line and the outlet of the sampling conduit is in selective fluid communication with the filling conduit, while the pneumatically conveyed stream is flowing through the sampling conduit, the receiving vessel is being filled with the proppant through the sampling conduit. Then, to perform the step of isolating the sampling conduit from the filling line of the receiving vessel, the method further includes isolating the inlet end and optionally, the outlet end of the sampling conduit from the filling line of the receiving vessel, effectively trapping a representative sample of the pneumatically conveyed sample in the sampling conduit. The method further includes emptying the material from the isolated sampling conduit, wherein the representative sample comprises the material emptied from the sampling conduit.

In some applications, it may be preferred to isolate only the inlet of the sampling conduit from the second conduit, thereby leaving the outlet of the sampling conduit in open communication with the second conduit. Since the inlet of the sampling conduit is isolated, material flowing through the second conduit typically does not flow backwards through the outlet of the sampling conduit in quantities large enough to contaminate the material captured in the sampling conduit. In those applications where small amounts of material flowing backwards from the second conduit into the sampling conduit will significantly affect the representative sample, the outlet of the sampling conduit is also isolated from the second conduit.

Alternatively, a preferred method includes venting the outlet end of the sampling conduit into the atmosphere. In this embodiment, while the stream of pneumatically transported solid particles is flowing through the sampling conduit, the receiving vessel is not being filled because the outlet of the sampling nozzle is not vented into the filling line of the receiving vessel. Optionally, the step of venting the outlet end of the sampling conduit into the atmosphere may include venting through a solids separation device and capturing the solids from the gas stream vented to the atmosphere, wherein the representative sample comprises both the material emptied from the sampling conduit and the solids captured by the solids separation device.

The present invention further provides a system suitable for performing the steps of the method for collecting a representative sample of a pneumatically conveyed stream of solid particles. In a preferred embodiment, the system includes a sampling conduit that is adapted for establishing a pneumatic flow of solid particles in a gas stream through the sampling conduit. Preferably, the sampling conduit comprises a smooth interior surface so that the solids do not adhere in grooves or crevices within the sampling conduit. The sampling conduit should be selected to ensure that erosion of the interior of the conduit does not contaminate the representative sample with material eroded from the interior of the conduit where such contamination may be a problem. The sampling conduit may be a metal pipe, flexible metal hose or may be made of plastic, rubber, synthetic rubber or other suitable materials known to those having ordinary skill in the art. Furthermore, the sampling conduit preferably has the same interior diameter as the filling line of the receiving vessel to minimize any disruptions to the flow of the stream of pneumatically conveyed solids and to ensure that the captured material is a representative sample of the material flowing through the filling line.

A preferred embodiment of the system of the present invention also includes means for diverting the entire stream of pneumatically conveyed solids through a second conduit, such as the filling line of the receiving vessel. A preferred embodiment further includes means for isolating the sampling conduit from the second conduit. It is preferred that the means for diverting the pneumatically conveyed stream be capable of activation substantially simultaneously with the means for isolating the sampling conduit so that the representative sample comprising the material in the sampling conduit may be captured without contamination of material that would not be representative of the flowing stream.

The means for diverting and isolating may include valves as well as diverters. To divert the stream from the sampling conduit into the second conduit, the inlet of the sampling conduit must be selectively closed and the inlet to the second conduit must be selectively opened so that the pneumatically conveyed stream is diverted from the sampling conduit to the second conduit. In one embodiment, valves may be placed at the inlet to each of the conduits. When the valve on the inlet to the sampling valve closes, the valve on the inlet to the second conduit opens so that the pneumatically conveyed stream is diverted from the sampling conduit to the second conduit.

The valves at the inlet to the sampling conduit and the inlet to the second conduit are preferably ball valves having the same diameter as the second conduit to minimize any disruptions to the flow of the pneumatically conveyed stream. Other valves may be suitable, such as gate valves, slide valves, plug valves, butterfly valves and others known to those having ordinary skill in the art. Preferably, the valves have steel bodies with valve seats and other internals that are suitable for the abrasive character of the pneumatically conveyed solids. Material selection of the valves and their components is dependent upon the nature of the pneumatically conveyed solids and is within the knowledge of those having ordinary skill in the art. Alternatively, the two valves on the inlets of the two conduits may be replaced with one three-way valve as known to those having ordinary skill in the art. Groups of valves may also be replaced with a diverter. A preferred diverter suitable for such service is more fully described below. The diverter may replace any number of valves on either the inlet or outlet ends of the sampling conduits and second conduit because one diverter may divert flow between two or more conduits.

The valves and/or the diverters may be manually operated but in a preferred embodiment, the valves and/or diverters are operated with actuators. The actuators may be powered by pneumatics, hydraulics, solenoids, springs, electric motors or combinations thereof. It is preferred that the valves and/or diverters be powered by actuators because it is important that the valves and diverters move quickly to minimize any disruption in the flow of the pneumatically conveyed stream and to ensure that a representative sample is captured in the sampling conduit.

In a preferred embodiment of the present invention, the system further includes a controller that signals the valves and/or the diverters to open and close. The controller may be an analog controller or it may be a digital controller as known to those having ordinary skill in the art. In a preferred embodiment, the controller is a computer, such as a personal or laptop computer, that is programmed to switch the valves and/or diverters at a specified time, after a specified time period, upon the input of a command or combinations thereof. Pressure sensors may be located at the inlet and/or outlet of one or more of the conduits, before and after one or more of the diverters/valves, at one or more locations along each of the conduits, or combinations thereof. One or more of the pressure sensors may be in electrical communication with the controller for monitoring and/or recording the pressure in the sampling system.

The valve or diverter on the inlet of the sampling conduit provides means to isolate the inlet of the sampling conduit from the second conduit but in a preferred embodiment, the system further includes means for venting the outlet of the sampling conduit into the second conduit. In such an embodiment, a valve or diverter is required on the outlet of the sampling conduit so that when the inlet valve or diverter on the sampling conduit is driven to the closed position, the valve or diverter on the outlet of the sampling conduit is also driven closed to isolate the outlet of the sampling conduit from the second conduit.

Optionally, the outlet of the sampling conduit may be vented to the atmosphere instead of venting to the second conduit. In a preferred embodiment, the sampling conduit is vented to the atmosphere through a solids separation device for capturing the solid particles carried from the outlet of the sampling conduit vented to the atmosphere. The solids separation device may be simple or complicated, depending upon the application. For example, the solids separation device may be a bucket, a vessel, a pressure vessel, a container, a cyclone, a receptacle or other device known to those having ordinary skill in the art that is capable of capturing the solids vented from the outlet of the sampling conduit. Preferably, the diameter of the vessel or container or other separation device will be large enough to significantly slow the velocity of the pneumatically conveyed stream of solid particles so that the particles separate from the gas stream exiting the separation device. Optionally, the gas stream may also be directed through a cyclone to further recover vented solids and thereby assure a representative sample is captured.

The present invention further provides a diverter that is useful for implementing the method and system of the present invention. The diverter of the present invention is useful for diverting and isolating the flow of the pneumatically conveyed fluids from one conduit to a second conduit selected from one or more conduits or from a conduit selected from one or more conduits to one conduit. While the following discussion focuses on the use of the diverter for proppants, the diverter of the present invention is not limited to a pneumatically conveyed proppant stream but is also useful for use with other pneumatically conveyed streams of solid particles as disclosed above.

In one preferred embodiment of the diverter, a flexible inlet conduit is adapted for being connected to a conduit in fluid communication with an unloading conduit from the proppant delivery vessel. A second end of the flexible inlet conduit is connected to an actuated slide having a single opening and is adapted for sliding into a position that aligns the single opening with a selected outlet conduit for the pneumatically conveyed solids to flow through. The slide blocks the other outlet conduits so the flow of the solids stream cannot flow through the other outlet conduits. The slide may be manually operated but in a preferred embodiment, the slide is operated with an actuator. The drive on the actuator may be hydraulic, pneumatic, an electric motor, a solenoid, a spring or combinations thereof or other driving force known to those having ordinary skill in the art.

An adjustable stop may be included to stop the slide at a predetermined position so the single opening on the slide is aligned with a selected outlet conduit. In a preferred embodiment, the adjustable stop is a calibrated stop post threadedly extended through the diverter body to stop the slide movement at predetermined positions. In some embodiments, an adjustable stop may be necessary for both sides of the diverter so that the slide may be stopped by one of the adjustable stops as the slide moves in a first direction and by a second adjustable stop when the slide moves in a second direction. Alternatively, the actuator may be calibrated to move the slide to a predetermined position to align the single opening on the slide with selected outlet conduits as known by those having ordinary skill in the art.

To divert the flow from the first selected outlet conduit to a second selected outlet conduit, the slide is positioned to align the single opening of the slide with the inlet of the second selected outlet conduit, thereby blocking the inlet to the first selected outlet conduit as well as any other unselected outlet conduits. In this manner, the flow of the pneumatically conveyed stream of proppants is diverted from one outlet conduit into another outlet conduit while at the same time, blocking the proppant from flowing into the first selected outlet conduit.

The diverter includes an attachment plate for connecting to the each of the outlet conduits. The slide slides along a sealing material on the inside surface of the attachment plate. In a preferred embodiment, the sealing material is DELRIN, a registered trademark of E.I Dupont de Nemours and Company, but other sealing materials may be used as known by those having ordinary skill in the art. In one embodiment, a housing containing the slide and attachment plate may be pressurized with air, or other suitable gas, to a pressure greater than the line pressure of the pneumatically conveyed stream so that any leakage between the slide and the seal material results in the gas flowing into the conduit rather than the solid particles into the housing. Alternatively, the housing may be open to the atmosphere or there may be no housing so that any leakage of solids falls to the ground for later retrieval. The pressure inside the housing may be maintained manually or may be controlled. The pressure may be controlled by using a self contained pressure regulator connected to the gas source to regulate the pressure inside the housing or by the controller using a pressure controller to send a control signal to a control valve or solenoid valve connected to the gas source.

Preferably, the inlet and outlet conduits are the same diameter as the inlet and outlet conduits of the system to which they are connected. The slide is preferably made of a material that is not eroded by the pneumatically conveyed solids. In a preferred embodiment, the slide is made of stainless steel. The conduits may be made of the same materials as disclosed above. Those parts of the diverter that are not exposed to the flowing stream of solids may be made of aluminum or other materials found suitable by those having ordinary skill in the art.

It should be noted that the discussion above was directed to using the diverter to divert a single inlet conduit into a selected outlet conduit selected from one or more outlet conduits. The diverter may also be used so that each of the outlet conduits as discussed above are inlet conduits and the single inlet conduit as discussed above is a single outlet conduit. In this manner, the diverter may be used to divert a selected inlet conduit selected from one or more inlet conduits into a single outlet conduit by simply attaching the side of the diverter with multiple connections to a selection of multiple inlet conduits and the side of the diverter with a single connection to an outlet conduit.

FIG. 1 is a schematic drawing of a system for collecting a representative sample of a pneumatically conveyed stream of solid particles having a sampling conduit vented to the receiving vessel fill line. A pneumatic truck 11 loaded with proppant is unloaded through an unloading hose 13 using air 12 to pneumatically convey the proppant to a storage hopper 22. The unloading hose 13 is connected to the inlet of the sampling device 20 useful for collecting a representative sample of the pneumatically conveyed proppant stream. The outlet of the sampling device 20 is connected to the inlet of the fill line 21 of the storage hopper 22. The sampling device 20 is connected with flanges 23 to the unloading hose 13 and the fill line 21. Alternatively, screwed connections, quick connect connections or other connections known to those having ordinary skill in the art may be used.

The sampling device 20 includes the sampling conduit 18 having an inlet valve 16 and an outlet valve 17 that are driven closed by the actuators 15 when the sampling conduit 18 is isolated from the sampling bypass line 19. The sampling device further includes an inlet valve 14 on the sampling bypass line 19 useful for switching the pneumatically conveyed proppants from the sampling conduit 18 to the sampling bypass line 19 and back again.

After the sampling device is in place, the flow of proppant is started by starting air 12 through the system to the hopper and then starting the flow of proppant from the pneumatic truck 11. With the sampling conduit isolation valves 16, 17 in an open position and the bypass valve 14 in a closed position, the proppant is pneumatically conveyed to the storage hopper 22. To capture a representative sample, the controller 26 sends a signal to the actuators 15 on the isolation valves 16, 17 to close and also sends a signal to the bypass valve 14 to open. The material captured in the isolated sampling conduit 18 is the representative sample and the proppant flow continues uninterrupted through the bypass line 19 to the storage hopper 22.

To collect the representative sample, the low point valve 25 on the sampling conduit 18 may be opened and the captured material drained into a vessel, such as a bucket or other convenient container (not shown) as the representative sample. Alternatively, the sampling conduit 18 may be disconnected from the quick connect couplings 24 and emptied to recover the representative sample from the isolated sampling conduit 18. As another alternative, a quick coupler (not shown) may be included at the low point of the sampling conduit 18 which, when uncoupled, allows the representative sample to be drained from the uncoupled portions of the sampling conduit 18.

Preferably, the bypass conduit 19 and the sampling conduit 18 are joined together in a sweeping configuration and not a configuration having right angles. Alternatively, plugged T's may be used for making 90° turns in the piping configuration as known to those having ordinary skill in the art. In some applications, 90° elbow piping components may be acceptable. The sweeping configuration provides less interruption to the flow of the pneumatically conveyed stream and minimizes the chances of plugging of the conduits. Optionally, pressure sensors 27 or pressure gauges may be installed on the inlet and outlet of both the bypass conduit 19 and the sampling conduit 18. Furthermore, signals from one or more of the pressure sensors 27 may be transmitted to the controller 26 to monitor and alarm pressure deviations as known to those having ordinary skill in the art. The controller 26 may also monitor time periods and divert the flow between the conduits 18, 19 after a set time period.

FIG. 2 is a schematic drawing of a system similar to the one shown in FIG. 1 but having optional diverters instead of valves. In a preferred embodiment of the invention, the valves 14, 16 on the inlet of the sampling conduit 18 and the inlet of the bypass conduit shown in FIG. 1 may be replaced with an inlet isolation diverter 28. Similarly, the outlet valve 17 shown in FIG. 1 may be replaced with an outlet isolation diverter 29. The inlet isolation diverter 28 may be positioned with an actuator 15, with the position of the diverter 28 controlled by the controller 26. The proppants enter the diverter 28 and exit either towards the sampling conduit 18 or the bypass conduit 19 depending on the position of the diverter 28. The proppant flowing from either the bypass conduit 19 or the sampling conduit 18 enters the outlet isolation diverter 29 and exits the diverter 29 into the fill line 21 of the storage hopper 22. The controller may also control the position of the exit isolation diverter 29 by sending a signal to the actuator 15 on the diverter 29.

When proppant is flowing through the sampling conduit 18, the inlet isolation diverter 28 is positioned to block flow to the bypass conduit 19 and to allow flow through the sampling conduit 18. The outlet isolation diverter 29 is positioned to allow flow from the sampling conduit 18 and block flow from the bypass conduit 19. When a sample is desired, the positions of the diverters 28, 29 are reversed to isolate the sampling conduit 18 and allow the pneumatically conveyed stream of proppants to flow through the bypass conduit 19 and on through the fill line 21 to the storage hopper 22. It should be noted that either or both of the diverters may be replaced with valves as shown in FIG. 1.

FIG. 3 is a schematic drawing of a system similar to the one shown in FIG. 1 but having two sampling conduits. In this embodiment of the present invention, two representative samples may be captured in the two sampling conduits 18. After flow is established in the first sampling conduit 18, the first sampling conduit may be isolated using the inlet diverter 32 to divert the flow from the first sampling conduit 18 to the bypass conduit 19. Essentially simultaneously, the outlet diverter 31 is positioned by the actuator 15 to divert the flow from the outlet of the first sampling conduit to the outlet of the bypass conduit 19. It should be noted that the outlet diverter 31 is optional for those applications that are not sensitive to a small amount of contamination of the representative sample by material flowing from the outlets of the conduits 18, 19 having an established flow into the outlets of the conduits 18, 19 that do not have an established flow.

When a second representative sample is desired, the diverter valves 32, 31 are positioned by the actuators 15 to establish a flow through the second sampling conduit 18. It should be noted that when using a diverter, the sampling conduits are preferably positioned so that the diverters 31, 32 need not open into a sampling conduit 18 that has already been used to capture a representative sample to prevent contamination of the previously captured representative sample.

It should be noted that in some applications, all three lines shown in FIG. 3 may be sample conduits 18. In such an embodiment of the present invention, three separate representative samples may be captured, one in each of the three sample conduits 18 as the unloading of the pneumatic truck 11 is accomplished through each of the three sample conduits 18, switching selectively through each of the three sample conduits 18 as the pneumatic truck 11 unloads. In this embodiment, a bypass conduit 19 is not necessary.

FIG. 4 is a schematic drawing of a system for collecting a representative sample of a pneumatically conveyed stream of solid particles having a sampling conduit vented to the atmosphere. In this embodiment of the present invention, the sampling conduit 18 is vented to the atmosphere through a vessel 39. As the pneumatically conveyed proppants enter the vessel 39, the velocity of the stream is slowed because of the larger diameter of the vessel 39. In some applications, the solid particles fully separate from the gas carrier, the gas exits the vessel 39 from the exit nozzle 41 and the representative sample is collected from the collection valve 38 at the bottom of the vessel 39.

In other applications of the present invention, a cyclone 37 may be preferred to further separate fine solid particles from the carrier gas exiting the vessel 37. The carrier gas with some fines enters the cyclone through the cyclone entrance 44, the carrier gas exits the vessel exit nozzle 41 and recovered fines flow down the dip leg 42 for recovery as part of the representative sample. A trickle valve 36 opens upon sufficient head pressure in the dip leg 42 to prevent carrier gas from bypassing the cyclone entrance 44. The representative sample may then be drained from the drain valve 38 located on bottom of the vessel 39.

It should be noted that in the embodiment of the invention shown in FIG. 4, the isolation valves 14, 16 on the inlet of the sample conduit 18 and the inlet of the sample conduit 19 may be replaced with a diverter 32 as discussed above and shown in FIG. 3.

FIG. 5 is an expanded view of a diverter useful for implementing the method and system of the present invention. The preferred diverters of the present invention disclosed herein are not meant to limit the choice of diverters or valves that may be used in the embodiments of the sampling system of the present invention. The diverter 50 of the present invention may be used for diverting and isolating the flow of a pneumatically conveyed fluid from one conduit to another conduit selected from one or more conduits. It may also be used to divert and isolate the flow of a pneumatically conveyed fluid from one conduit selected from one or more conduits to another single conduit. In the following description, the diverter 50 is described as diverting a pneumatically conveyed stream from one conduit to one selected from more than one outlet conduits but it should be noted that the diverter may be used in reverse equally effectively.

The diverter 50 includes a connection 51 that is adapted for being connected in fluid communication with an unloading conduit of a delivery vessel. The connection 51 may be flanged, a quick connect, a screwed connection or other connection type known to those having ordinary skill in the art. In one preferred embodiment, the inlet connection is preferably attached to a length of flexible conduit 52, such as, for example, metal hose. The flexible conduit 52 may be clamped to the slide nozzle 56 using a hose clamp 57 or by other means such as, for example, a screwed connection, quick connect, flange or other means known to those having ordinary skill in the art.

The diverter 50 further includes a slide 58 with a single opening 71 that is slidingly disposed between the intake flange 53 and the exhaust flange 60. A sealing material 59 is disposed between the slide 58 and the exhaust flange 60 for providing a seal between the slide 58 and the inlets of the outlet conduits 64, 65.

The exhaust flange 60 includes outlet nozzles 61, 62 that are coupled to outlet conduits 64, 65 with clamps 63 or by other means such as, for example, a screwed connection, quick connect, flange or other means known to those having ordinary skill in the art. The outlet conduits 64, 65 further include connections 51 for coupling to the system conduit, such as the fill line of the storage hopper (not shown). A top cover 54 may be included to protect personnel from the sliding action of the slide 58. The slide 58 may be manually operated or may be attached to an actuator (not shown) by the actuator arm 55 to position the slide 58 to divert a pneumatically conveyed stream of solid particles to a selected outlet conduit 64, 65. Preferably, the actuator is set to position the slide 58 at the predetermined locations of the inlets to the outlet conduits 61, 62.

Figure 6:
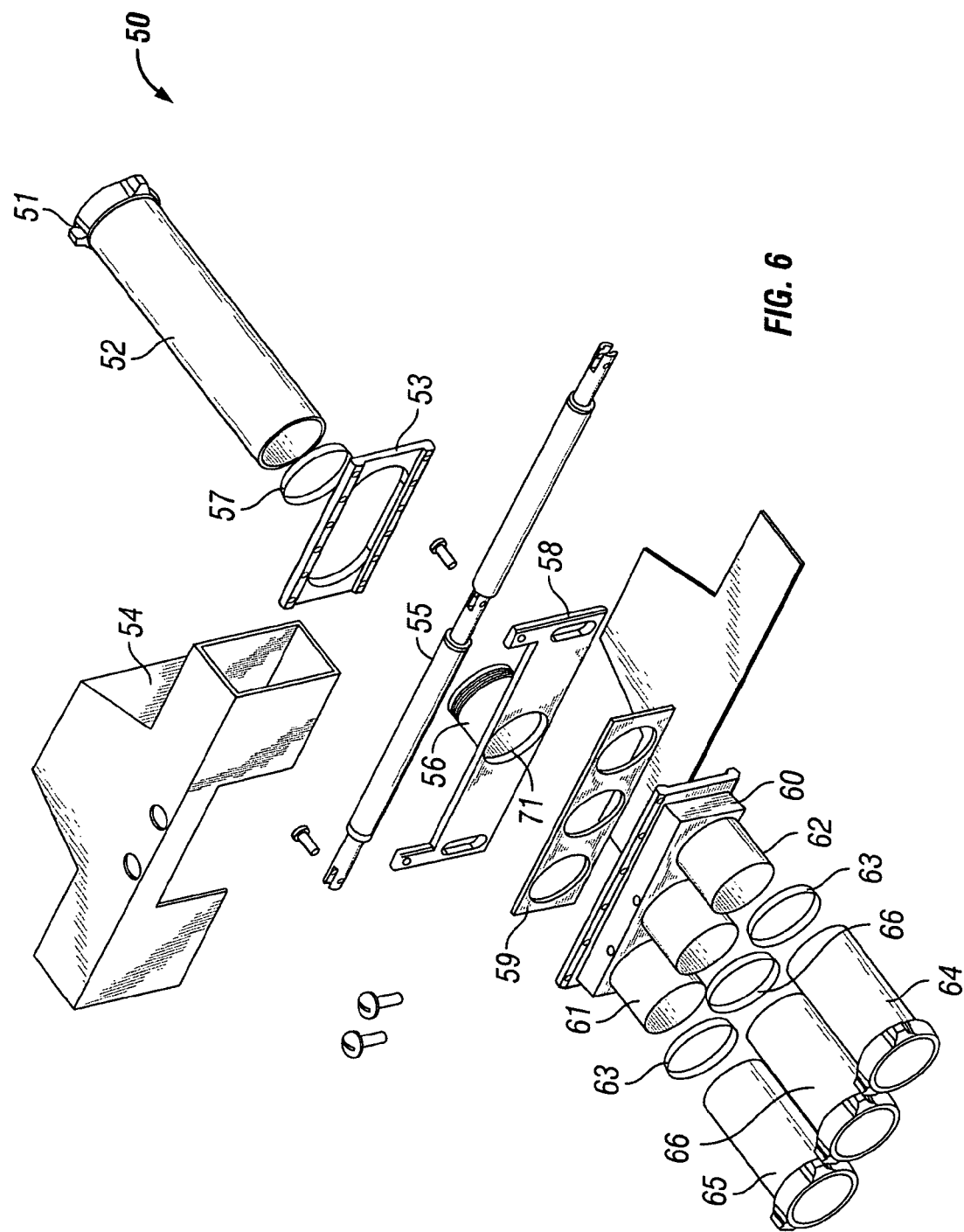
FIG. 6 is an expanded view of a diverter useful for implementing the method and system of the present invention having more than two conduits on one side of the diverter.

FIG. 6 is an expanded view of a diverter useful for implementing the method and system of the present invention having more than two conduits on one side of the diverter. In this embodiment of the diverter 50, an additional outlet conduit 67 is included to demonstrate that multiple conduits may be included on one side of the diverter. It should further be noted that the multiple conduits 64, 65, 66 on one end of the diverter may be either inlet conduits diverting the flow to a single outlet conduit 52 or a single inlet conduit 52 diverting the flow to one of several outlet conduits 64, 65, 66.

Figure 7:
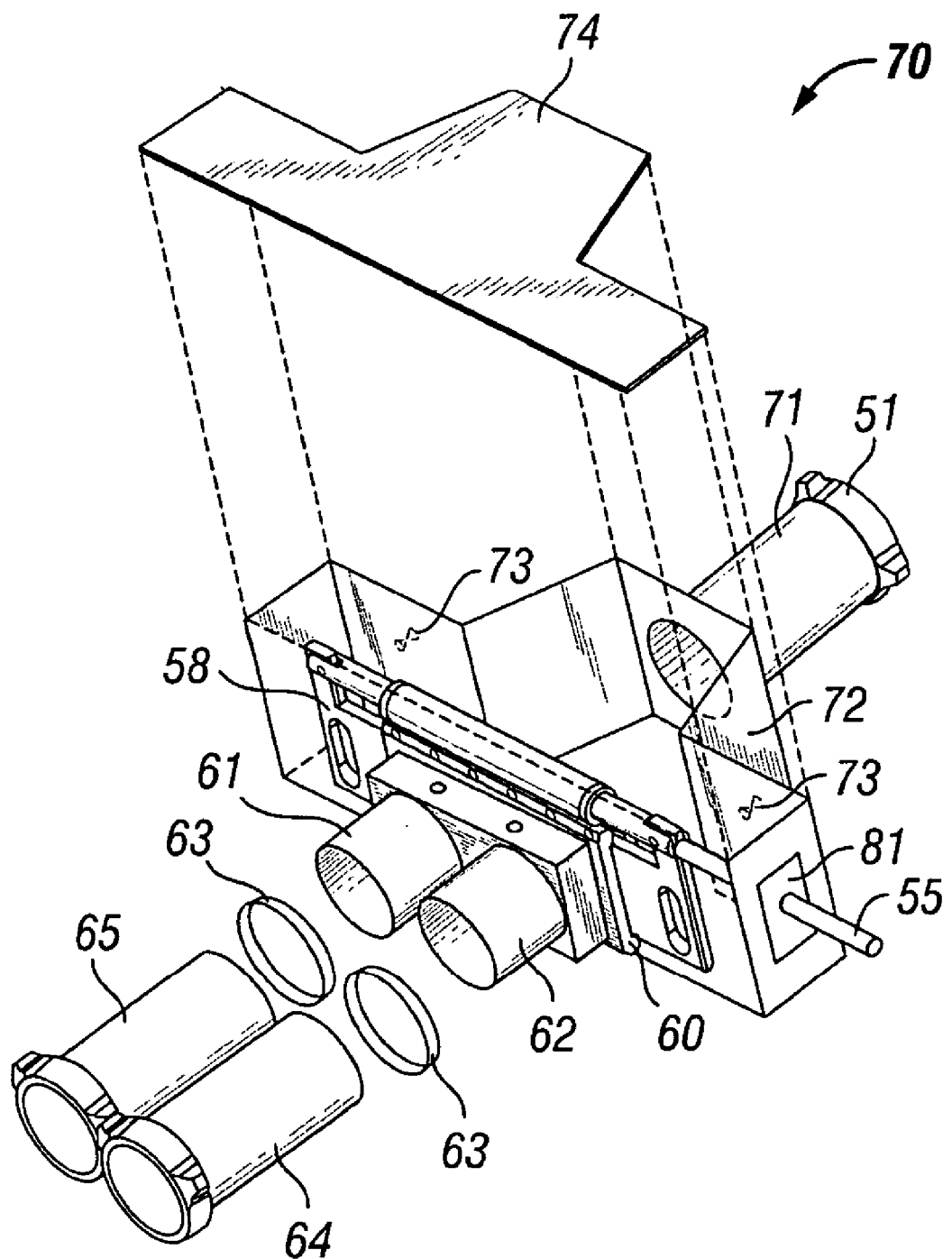
FIG. 7 is a perspective view of a diverter useful for implementing the method and system of the present invention having a pressurized housing.

FIG. 7 is an expanded view of a diverter useful for implementing the method and system of the present invention having a pressurized housing without a flexible conduit connected to the slide. In an embodiment of a diverter 70 having a pressurized housing 72, an inlet nozzle 71 is welded to the housing 72 and is adapted for connecting to the piping system in fluid communication with the pneumatic truck 11 shown in FIG. 2. A quick connect coupling 51 is provided for connecting to the unloading system piping but other connection types may be suitable as discussed above.

The housing 72 is suitable for being pressurized to a pressure at least as high as the pressure of the pneumatically conveyed stream of solid particles and is therefore, preferably of welded or cast construction. Carbon steel is a preferred material though other suitable materials are useful as known to those having ordinary skill in the art. The housing 72 is typically connected to the exhaust flange 60, either by welding, by casting or preferably, the housing may be bolted to the exhaust flange with a suitable gasket material (not shown) therebetween. Preferably, the housing top 74 is removable to provide access to the diverter 70 interior and may be flanged or otherwise bolted (not shown) to the housing 72.

To prevent stagnant areas within the housing 72, air purges 73 are provided to blow solid materials from areas wherein the solid particles could settle and become stagnant, thereby preventing the operation of the slide 58.

The actuator arm 55 extends through the housing 72 through a packing gland 81 or other suitable sealing means. The actuator arm 55 is attached to an actuator (not shown) to move the slide to the preferred positions. Alternatively, the slide 58 itself may slide through a packing gland mounted on each side of the diverter 70 so that solid material cannot block the slide operation by packing into the area between the slide and the housing interior sidewall.

Figure 8:
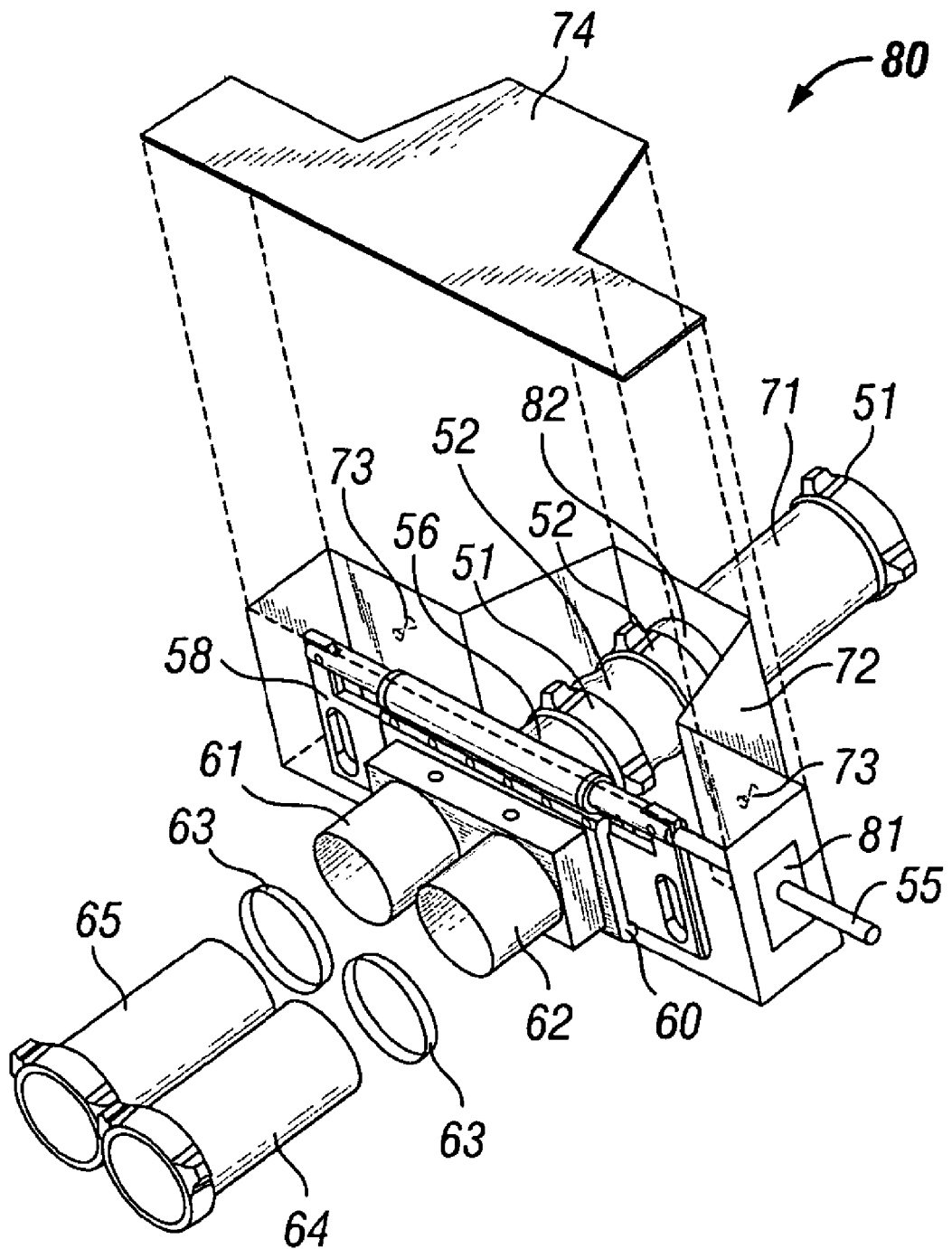
FIG. 8 is a perspective view of a diverter similar to the one shown in FIG. 7 except having a flexible conduit within a pressurized housing.

FIG. 8 is an expanded view of a diverter useful for implementing the method and system of the present invention having a pressurized housing with a flexible conduit connected to the slide. This embodiment of the present invention provides a diverter 80 having a pressurized housing 72 similar to the one shown in FIG. 7, except a flexible conduit 52 is attached to an interior nozzle 82 and to the slide nozzle 56. With the housing 72 pressurized to a pressure greater than the pressure in the inlet nozzle 71, any leakage around the slide 58 would be pressurized gas from the housing 72 into the outlet conduits 64, 65 rather than solid particles from the pneumatically conveyed stream into the housing 72 or the atmosphere. The air purges 73 may be connected to a pressure regulator to control the pressure inside the housing or the air purges 73 may be manually adjusted.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. For example, the phrase "a solution comprising a phosphorus-containing compound" should be read to describe a solution having one or more phosphorus-containing compound. The terms "at least one" and "one or more" are used interchangeably. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

It should be understood from the foregoing description that various modifications and changes may be made in the preferred embodiments of the present invention without departing from its true spirit. The foregoing description is provided for the purpose of illustration only and should not be construed in a limiting sense. Only the language of the following claims should limit the scope of this invention.

What is claimed is:

1. A method for obtaining a representative sample of solid particles from a pneumatically conveyed stream of the solid particles, comprising:
   establishing a pneumatic flow of solid particles in a gas stream through a sampling conduit by venting an outlet end of the sampling conduit into a second conduit;
   diverting the stream through the second conduit; and
   isolating the sampling conduit from the second conduit substantially simultaneously with the step of diverting the stream through the second conduit by isolating the outlet end of the sampling conduit from the second conduit.

2. The method of claim 1, further comprising the step of:
   emptying material from the isolated sampling conduit, wherein the representative sample comprises the material emptied from the sampling conduit.

3. The method of claim 1, wherein the solid particles are a proppant.

4. A system for obtaining a representative sample of a pneumatically conveyed stream of solid particles, comprising:
   a sampling conduit adapted for establishing a pneumatic flow of solid particles in a gas stream through the sampling conduit;
   means for diverting the stream through a second conduit;
   means for venting an outlet end of the sampling conduit in the second conduit;
   means for isolating an inlet of the sampling conduit from the second conduit substantially simultaneously with activating the means for diverting the stream through the second conduit; and
   means for isolating the outlet end of the sampling conduit from the second conduit.

5. The system of claim 4, further comprising:

means for emptying material from the isolated sampling conduit, wherein the representative sample comprises the material emptied from the sampling conduit.

6. The system of claim 4, wherein the solid particles are a proppant.

7. The system of claim 4, further comprising:

a controller for controlling a position of the means for diverting the stream through a second conduit, the means for isolating an inlet sampling conduit, or combinations thereof.

* * * * *